United States Patent [19]

Palestrant

[11] Patent Number: 4,930,525
[45] Date of Patent: Jun. 5, 1990

[54] METHOD FOR PERFORMING C.T. GUIDED DRAINAGE AND BIOPSY PROCEDURES

[76] Inventor: Aubrey M. Palestrant, 6800 N. 47th St., Paradise Valley, Ariz. 85253

[21] Appl. No.: 329,800

[22] Filed: Mar. 28, 1989

[51] Int. Cl.⁵ ............................................. A61B 17/00
[52] U.S. Cl. ................................... 128/898; 604/116; 606/108
[58] Field of Search ................. 128/898, 899; 604/116; 606/108

[56] References Cited

U.S. PATENT DOCUMENTS

| | | |
|---|---|---|
| 2,409,432 | 10/1946 | Hubbard . |
| 2,451,183 | 10/1948 | Tantimonaco . |
| 4,058,114 | 10/1977 | Soldner . |
| 4,212,297 | 7/1980 | Frosch et al. . |
| 4,341,220 | 7/1982 | Perry ................................... 128/630 |
| 4,583,538 | 4/1986 | Onik et al. . |
| 4,592,352 | 6/1986 | Patil . |
| 4,733,661 | 3/1988 | Palestrant . |

OTHER PUBLICATIONS

Frederick et al., "A Light-Guidance System to be Used for CT-Guided Biopsy", *Radiology*, vol. 154, No. 2, Feb. 1985, pp. 535-536.
Hruby et al., "A New Device for CT-Guided Biopsy and Puncture: Experimental and Clinical Data", Scientific Program of the *Radiological Society of North America*, Dec. 1986, Works in Progress-General Diagnosis Abstracts, vol. 161 (P), p. 347.

*Primary Examiner*—Stephen C. Pellegrino
*Attorney, Agent, or Firm*—Cahill, Sutton & Thomas

[57] ABSTRACT

A guidance method for use in conjunction with a C.T. scanner allows a user to accurately place a drainage catheter, biopsy needle, or like catheter within a patient's body. A scan of the patient's body is made using the C.T. scanner to form a cross-sectional image of the target area within the patient's body. An insertion path is selected on the scanned cross-sectional image to reach the target area, and the lateral distance is determined between the vertical axis of the scanned image and the insertion site. The insertion angle and insertion distance along the insertion path are also computed from the cross-sectional image. The lighting system of the C.T. scanner projects a laser-generated longitudinal reference beam on to the patient's body corresponding with the vertical axis of the scanned image; the lighting system further projects at least one transverse beam on to the patient's body for designating the vertical plane through which an image was scanned. The insertion site is located by measuring upon the patient's body, along the transverse reference beam, the aforementioned lateral distance, starting from the longitudinal reference beam. The insertion site is marked, and th tip of the catheter is advanced into the insertion site, while maintaining the catheter within the transverse reference beam. The catheter is maintained at the computed insertion angle relative to a horizontal plane, and the catheter is advanced by the computed insertion distance to reach the target area.

7 Claims, 2 Drawing Sheets

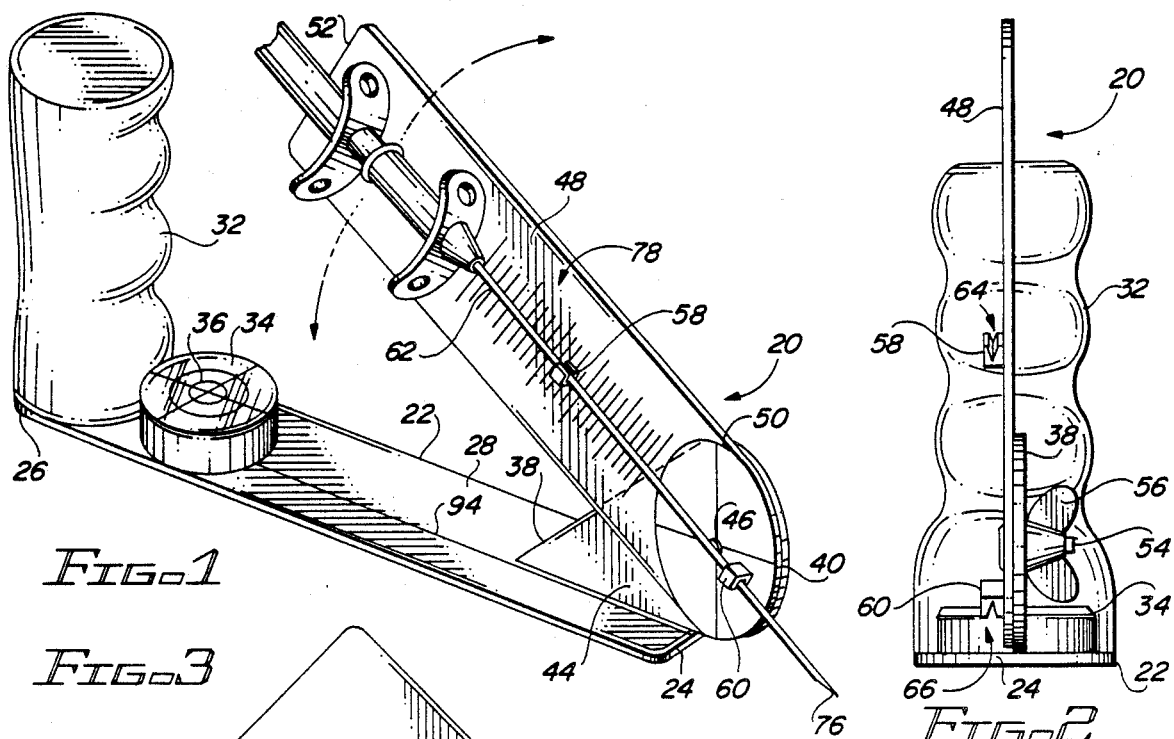
FIG-1
FIG-3
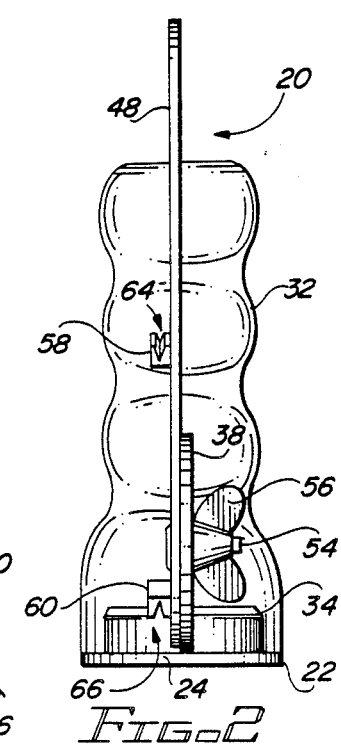
FIG-2
FIG-4
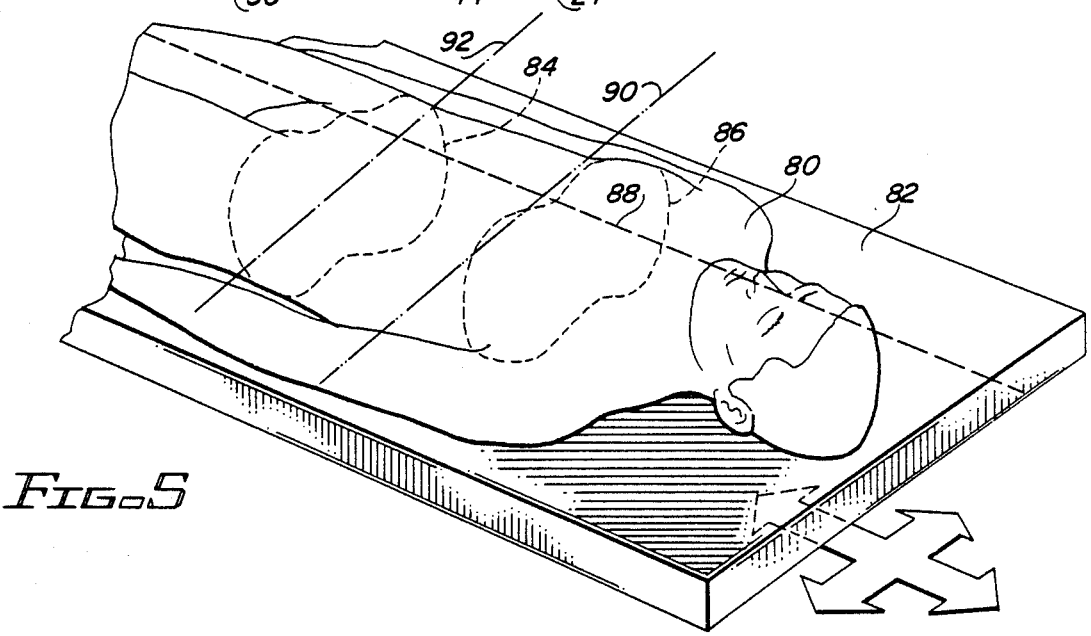
FIG-5

METHOD FOR PERFORMING C.T. GUIDED DRAINAGE AND BIOPSY PROCEDURES

CROSS-REFERENCE TO RELATED APPLICATIONS

The present application describes and claims subject matter that is, at least in part, disclosed in applicant's earlier filed patent application Ser. No. 042,728, filed Apr. 27, 1987, and issued as U.S. Pat. No. 4,733,661, on Mar. 29, 1988. The present application is not co-pending with applicant's aforementioned application Ser. No. 047,728, and no claim is made to the benefit of the earlier filing date thereof.

BACKGROUND OF THE INVENTION

1. Field of the Invention

The present invention relates generally to methods for guiding a catheter or needle to a preselected point within a patient's body, and more particularly, to a method for guiding biopsy needles, drainage catheters and the like, into a patient's body in conjunction with a C.T. scanner.

2. Description of the Prior Art

In recent years, total body C.T. scanners have become commonly used to provide doctors with a cross-sectional picture of a patient's internal organs and tissues. This imaging modality can define abnormal tissues but, in many situations, cannot determine what has caused the abnormality. Through the use of C.T. scanner technology, physicians are able to accurately place biopsy needles and drainage catheters into abnormal tissues with a high degree of success and with a low morbidity and mortality to the patient This approach has changed the way in which medical diagnoses are made. For example, exploratory laparotomies for suspected tumors have decreased significantly in recent years in view of the increasing use of C.T. guided biopsies of suspicious masses in the abdomen.

C.T. scanners that are presently available are capable of measuring a proposed trajectory for a biopsy needle or drainage catheter to within 0.1 millimeters with respect to depth, and within 0.1 degree with respect to angular orientation. However, there are no known methods available, apart from the method disclosed in applicant's U.S. Pat. No. 4,733,661, which can accurately and easily utilize such information to properly position a biopsy needle or drainage catheter relative to the patient's body. To the applicant's knowledge, most physicians perform C.T. guided procedures by initially positioning the needle or catheter at a rough estimation of the desired angle, and by then slowly advancing the needle or catheter into the patient's body, taking numerous C.T. scans along the way to determine the actual position of the needle or catheter, and altering its trajectory as needed. This trial and error technique has major disadvantages. First, it usually requires a relatively long period of time and causes the patient to remain in a fixed position which most patients find uncomfortable. Secondly, additional radiation may be harmful to the patient. Additionally, in institutions where C.T. access is limited, a lengthy procedure may excessively utilize the available time, preventing other patients from being studied.

C.T. scanner guided stereotactic brain surgery is known in the art, and various patents disclose frames for attachment to a patient's head for performing a stereotactic surgical procedure. Such stereotactic surgical apparatus for use in conjunction with C.T. scanners is disclosed in U.S. Pat. No. 4,341,220 and U.S. Pat. No. 4,592,352. The brain, because of its consistent relationship to the boney skull, can have a rigid frame attached to it which can then provide the needed reference coordinates from which various paths can be calculated. However, with respect to other parts of the body, underlying organs and tissues do not bear a constant relationship to the surface anatomy. In addition, parts of the body other than the head lack a sufficiently rigid structure to which a stereotactic frame can be reliably attached.

U.S. Pat. No. 4,058,114 to Soldner discloses a guide aide designed to introduce a puncturing cannula into the body under the guidance of ultrasound imaging equipment. The disclosed apparatus requires that the guide aide be secured to the ultrasound transducer. The disclosed apparatus further requires a targeting aide fastened to the ultrasound image viewing screen. The ultrasound transducer rests upon the patient's body and provides a support for the guide aide. In contrast, C.T. scanners do not utilize a transducer in contact with the patient's body, and accordingly, the guide aide and targeting aide disclosed by Soldner could not be used in conjunction with C.T. guided interventional procedures.

U.S. Pat. No 4,583,538 issued to Onik et al. discloses an apparatus designed to facilitate C.T. guided biopsies of the body. The stereotaxis guide instrument disclosed in this patent is floor-mounted and is designed to position a needle guide by moving the same through any of three perpendicular axes. Angular rotations about such axes are permitted to orient the needle guide in any desired direction. However, the articulated arm configuration disclosed by Onik et al. requires the user to manipulate a great number of cranks, bearings, and arms before a needle can be inserted into the patient.

The aforementioned patent to Onik further discloses a method for placing probes in a body based on images from a C.T. scanner. The method disclosed in the Onik patent consists of placing a localizer device made of carbon fiber on the patient's body to cause the localizer device to appear in the C.T. scanned image. The localizer device includes a base which must be aligned parallel to the C.T. scanning plane. A first scan is made through a first scan plane to locate a reference point on the scanned image corresponding to an edge of the localizer device in the scanned plane A skin entry point is also located on the scanned image and the distances between the reference point and the skin entry point along x and y axes are measured. A second scan is made through the target area in the patient's body. Coordinates for the positions of the skin entry point and target point, along the x, y, and z axes, are determined, and the azimuth, angle of declination, and needle path length are calculated. The Onik patent specification further states that the scan plane of the skin entry point and the scan plane of the target area may be in the same plane. While the above-described method disclosed by Onik is technically accurate, the use of the aforementioned localizer device, and the need to locate the same within a scanned image to generate a reference point, is believed to unnecessarily complicate such method.

C.T. scanners are adapted to project a laser-generated longitudinal reference beam along the central longitudinal axis of the scanning table. This longitudinal reference beam serves to designate, upon the patient's body, the vertical axis of all scanned images generated by the C.T. scanner. C.T. scanners are also adapted to project a first laser-generated transverse reference beam within the gantry of the scanner and perpendicular to the longitudinal reference beam to indicate the actual portion of the patient's body through which a scan is being taken. A second transverse reference beam is also projected by the C.T. scanner outside the gantry and parallel to the first transverse beam and spaced therefrom by a predetermined distance. Once a target area in the patient's body has been scanned, the scanning table can be moved along the longitudinal axis by the predetermined distance to cause the second transverse beam to illuminate the same portion of the patient's body that was previously illuminated by the first transverse beam before the scanning table was moved. Applicant has determined that the aforementioned longitudinal reference beam and transverse reference beams may be used to quickly and accurately guide a biopsy needle, drainage catheter, or the like, toward the target area without the need for a localizer device of the type described by Onik.

Accordingly, it is an object of the present invention to provide a guidance method which allows a physician or other user to perform a C.T. guided interventional procedure within a patient's body accurately, easily and more expeditiously than methods used in the past to perform such procedures.

It is another object of the present invention to provide such a guidance method which eliminates the need to make repeated C.T. scans in order to insure that the biopsy needle or drainage catheter is correctly aimed toward the target area.

It is a further object of the present invention to provide such a guidance method which permits the ready identification of an insertion site upon the patient's body without requiring the attachment of a localizer device to the patient's body and without requiring the scanning of such a localizer device.

It is a still further object of the present invention to provide such a guidance method wherein a physician or other user can easily and continuously maintain the catheter within the plane of the patient's body that was scanned by the C.T. scanner to locate the target area.

These and other objects of the present invention will become more apparent to those skilled in the art as the description thereof proceeds.

SUMMARY OF THE INVENTION

Briefly described, and in accordance with a preferred embodiment thereof, the present invention is a guidance method for use in conjunction with a C.T. scanner and allowing a user to accurately place a biopsy needle, drainage catheter, or the like within the body of a patient quickly, conveniently and accurately. The C.T. scanner is adapted to project a longitudinal reference beam along the central longitudinal axis of the C.T. scanner and upon the patient's body to indicate the vertical axis of the scanned cross-sectional images formed by the C.T. scanner. The C.T. scanner is also adapted to project at least one transverse reference beam of light across the patient's body to indicate the location of the vertical scan plane through which the patient's body has been scanned to form a particular cross-sectional image. The present invention includes the step of scanning the patient's body using the C.T. scanner to form a cross-sectional image of the target area within the patient's body at which the catheter is to be directed. The user selects a desired insertion path on the scanned cross-sectional image along which the catheter is to be guided. The user then measures or otherwise determines the distance upon the cross-sectional image from the point at which the vertical axis of the scanned image intersects the skin or outer surface of the patient's body to an insertion site, the insertion site corresponding to the intersection of the desired insertion path with the skin or outer surface of the patient's body. The user then measures the aforementioned distance, using a ruler or other measuring instrument, upon the patient's body along the transverse reference beam, beginning from the longitudinal reference beam, and marks the insertion site upon the patient's body. The piercing tip of the catheter is then inserted into the patient's body at the marked insertion site, while the user positions the catheter to lie within the plane of the transverse reference beam whereby the length of the catheter is illuminated thereby. The catheter is then advanced toward the target area while maintaining the catheter fully illuminated by the transverse reference beam to ensure that the catheter is maintained within the vertical plane that was scanned by the C.T. scanner.

Preferably, the present method includes the step of measuring the angle upon the cross-sectional C.T. scanner image which the selected insertion path forms relative to the horizontal axis of the cross-sectional image. Having computed this insertion angle, the user maintains the catheter at the same insertion angle, relative to a horizontal plane, as the catheter is guided into the patient's body. Similarly, the user can measure, or otherwise compute, the insertion distance upon the cross-sectional C.T. scanner image from the insertion site on the outer surface of the patient s body to the target area. During insertion of the catheter, the user monitors the length of the catheter which has been inserted into the patient's body and advances the catheter until it has been inserted by the desired insertion distance.

BRIEF DESCRIPTION OF THE DRAWINGS

FIG. 1 is a perspective view of a guidance device useful in practicing the present invention.

FIG. 2 is an end view of the guidance device shown in FIG. 1.

FIG. 3 is a side view of the guidance device shown in FIG. 1 wherein a handle has been omitted.

FIG. 4 is a partial top view of the left most portion of the guidance device shown in FIG. 3, including a circular bubble level affixed thereto.

FIG. 5 is a perspective view of a patient lying upon a C.T. scanning table and wherein reference beams of laser light projected by the C.T. scanner are indicated.

DETAILED DESCRIPTION OF THE PREFERRED EMBODIMENT

Figure 6:
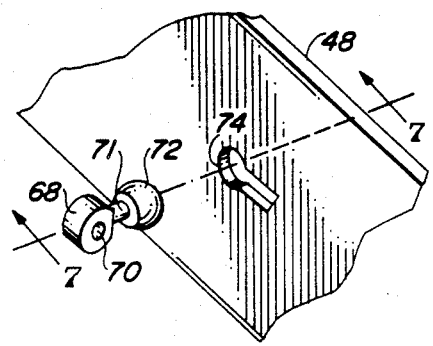
FIG. 6 is a partial view of the needle support arm of the guidance device illustrating a needle guide releasably secured thereto.

With reference to FIG. 1, a guidance device is identified generally by reference numeral 20 including a generally planar base 22 having a first end 24, an opposing second end 26, and a longitudinal axis extending therebetween. planar base 22 includes an upper planar surface 28 and an opposing lower surface 30 (see FIG. 3). As shown in FIGS. 1 and 2, a handle 32 may be provided at end 26 of planar base 22, handle 32 being contoured to the user's grip for allowing the user to support guidance device 20 in position relative to a patient's body.

As shown in FIGS. 1–4, a circular bubble level 34 is secured to upper surface 28 of planar base 22 proximate second end 26 thereof. Bubble level 34 includes a bullseye 36 for indicating to a user that planar base 22 is lying in a horizontal plane.

Guidance device 20 also includes a vertical support 38 secured to upper surface 28 of planar base 22 adjacent first end 24 thereof and extending perpendicularly to planar base 22. The right-most (relative to FIG. 3) end 40 of vertical support 38 preferably extends beyond first end 24 of planar base 22 and has a semi-circular contour Angle markings 42 are formed upon the inner surface 44 of vertical support 38 along the semi-circular periphery of right most end 40 in order to provide a protractor. The radial center of the aforementioned protractor is indicated by reference numeral 46.

As shown in FIGS. 1–3, a needle support arm 48 extends between a first end 50 and a second end 52 and is substantially planar First end 50 is preferably semi-circularly shaped and has the same radius of curvature as semi-circular end 40 of vertical support 38. Needle support arm 38 is pivotally coupled to end 40 of vertical support 38, the pivotal coupling aligning the radial center of semi-circular end 50 with the radial center 46 of semi-circular end 40. In this manner, needle support arm 48 is maintained perpendicular to planar base 22 and is free to pivot with respect thereto. As shown in FIG. 2, the pivotal coupling between needle support arm 48 and vertical support 38 may be made by a screw 54 passing through aligned holes (not shown) formed in the needle support arm 48 and vertical support 38. Preferably, screw 54 is engaged by a wing nut 56 which, when tightened, locks needle support arm 48 at a predetermined angle relative to planar base 22. Screw 54 passes along the horizontal pivot axis about which needle support arm 48 pivots. This pivot axis lies generally perpendicular to the longitudinal axis of base 22.

In order to permit a user to view the angular markings 42 forming the protractor, semi-circular end 50 of needle support arm 48 is preferably made of a transparent material. A reference line 58 passing through pivotal coupling point 46 and extending along the longitudinal axis of needle support arm 48 is provided for allowing the user to read off from the protractor the present angle of needle support arm 48 relative to planar base 22.

The guidance device shown in FIGS. 1–3 is intended to slidingly support a biopsy needle. drainage catheter. or the like upon needle support arm 48. In this regard, a pair of needle guides 58 and 60 are secured to needle support arm 48 for slidingly supporting a biopsy needle, drainage catheter, or the like. Within FIG. 1, a biopsy needle, designated by reference numeral 62, is shown supported by needles guides 58 and 60 for sliding movement along the longitudinal axis of biopsy needle 62. In this manner, a user can slide the shaft of needle 62 along guides 58 and 60 and guide the needle 62 into the patient's body at a desired angle.

As noted above. the guidance device should be easily disengaged from the needle once the needle is properly placed within the patient's body. For example, a physician or other user of the guidance device would probably find it difficult to efficiently operate the biopsy needle in order to obtain a tissue sample if the needle were engaged with the guidance device.

Figure 8:
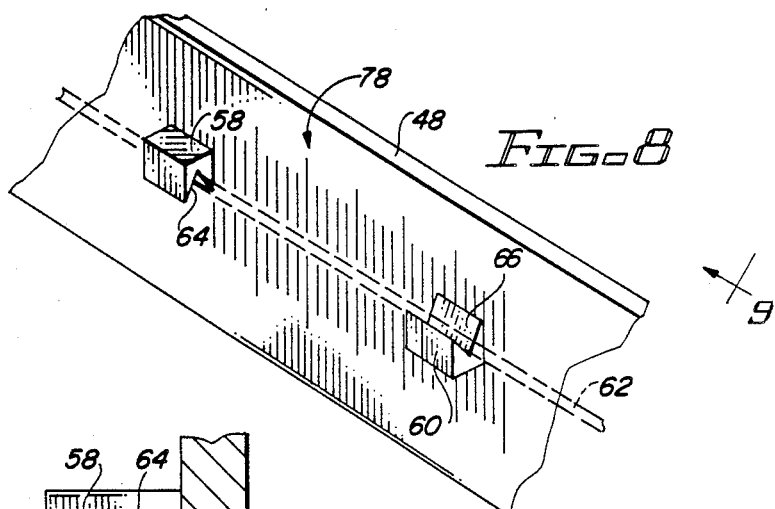
FIG. 8 is a perspective view of a portion of the needle support arm including a pair of offset needle guides directed in opposing directions.

Accordingly, the guidance device shown in FIGS. 1–3 provides needle guide 58 secured to needle support arm 48 at a first point and including a first V-shaped engagement surface 64 forming a channel opening outward in a first direction for slidingly engaging one side of needle 62. Needle guide 60 is secured to needle support arm at a second point spaced apart from needle guide 58 and proximate first end 50 of needle support arm 48. Needle guide 60 also includes a V-shaped engagement surface 66 forming a channel which opens outwardly in a direction opposite to that for engagement surface 64, as shown in FIG. 8. By continuously maintaining the walls of needle 62 engaged with surfaces 64 and 66, as shown in FIG. 9, the user can easily maintain the needle 62 at the desired angle while sliding the same towards its target.

Figures 7, 9:
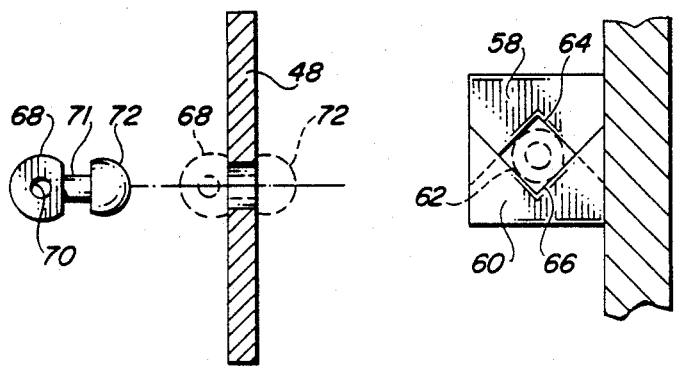
FIG. 7 is a sectional view of the needle support arm shown in FIG. 6 taken through lines 7—7.
FIG. 9 is an end view of the needle support arm shown in FIG. 8 viewed from lines 9—9.

FIGS. 6 and 7 show an alternate form of needle guide which may be used in conjunction with needle support arm 48. As shown in FIG. 6, needle guide 68 includes a hole 70 Which is of a size that just permits the shaft of the biopsy needle or drainage catheter 62 to be slidingly passed therethrough. Needle guide 68 includes an enlarged tab 72 connected by a reduced width portion 71. Tab 72 is adapted to be inserted within a slightly oversized hole 74 formed in needle support arm 48. A reduced width channel 75 extends from oversized hole 74 and is adapted to slidingly receive portion 71 of needle guide 68 to releasably lock needle guide 68 to needle support arm 48. Preferably, a pair of such needle guides 68 are releasably secured to needle support arm 48 at spaced apart points lying along the longitudinal axis of the needle support arm 48. The biopsy needle or drainage catheter is caused to pass simultaneously through both of such needle guides to maintain the needle or catheter in proper alignment with needle support arm 48. Once the needle has been placed within the patient, needle guides 68 are slid out of channels 75 and are then released from their cooperating holes 74 in support arm 48, and the remainder of the guidance device is removed, leaving only needle guides 68 in engagement with the shaft of needle 62.

The guidance device shown in FIGS. 1–3 is preferably designed to allow a physician or other user to determine the insertion distance to which the tip 76 of biopsy needle 62 has been inserted into the patient's body. For this purpose, periodic graduations, such as centimeter markings, designated generally by reference numeral 78 are printed or otherwise marked upon needle support arm 48. By noting a fixed point upon the needle or catheter, and its relation to the graduations 78, the user can accurately gauge the depth to which the tip of the needle or catheter has been inserted.

Referring now to FIG. 5, a patient 80 is shown lying upon a movable, computer-controlled scan table 82 of a C.T. scanning system, such as a GE 9800 C.T. scanner commercially available from General Electric, or other high resolution C.T. scanner. Other components of the C.T. scanning system are omitted for clarity. The C.T. scanner is designed to provide a cross-sectional image of the patient's body taken through a vertical scan plane. Two such vertical scan planes are shown in FIG. 5 by dashed lines 84 and 86.

As a reference aide, C.T. scanners include a C.T. lighting system designed to project reference beams of laser light toward the scanning table and upon the patient's body to indicate the portion of the patient's body being scanned. A first reference beam, indicated by dashed line 88, is projected longitudinally along the center of scanning table 82 to indicate the center point, or vertical axis, of the scanned image. A first transverse beam of laser light, designated by dashed line 90, is projected by the C.T. scanner within the gantry of the scanner (not shown) to indicate the location of the vertical plane through which the patient's body is being scanned. A second transverse beam of laser light, indicated by dashed line 92, is projected by the C.T. scanner outside the scanner gantry a known distance apart from, and parallel to, the first transverse beam 90. This second transverse beam of laser light is provided principally to aid a technician or physician in properly positioning the patient's body for scanning before the scanning table is actually advanced into the scanner. It is often difficult for a physician to insert a biopsy needle within the patient's body without moving the scanning table out of the scanning apparatus. Accordingly, the scanning table 82 may be withdrawn from the scanning apparatus by the known distance separating transverse beams 90 and 92 in order to cause transverse beam 92 to overlie the area of the patient's body that was scanned just immediately prior to the movement of scanning table 82.

To help insure that the biopsy needle, drainage catheter or like device will hit its intended target, it is desirable for the user to maintain the needle or catheter within the vertical plane that was viewed by the C.T. scanner to locate the target. In this regard, a reference line 94 is formed upon upper surface 28 of planar base 22 extending substantially between first end 24 and second end 26 thereof. Reference line 94 is positioned to lie within the vertical plane that contains the biopsy needle 62 supported by needle support arm 48. In other words, reference line 94 coincides with the vertical projection of biopsy needle 62 onto planar base 22. During use of guidance device 20, the user positions planar base 22 so as to maintain reference line 94 in alignment with transverse laser light beam 92 (see FIG. 5), while simultaneously maintaining planar base 22 horizontal, thereby insuring that needle 62 lies within the vertical plane of the patient's body that was sectioned by the C.T. scanner. In practice, because needle 62 is above reference line 94, the transverse laser light beam will illuminate the length of needle 62 before needle 62 is inserted into the patient's body.

Figure 10:
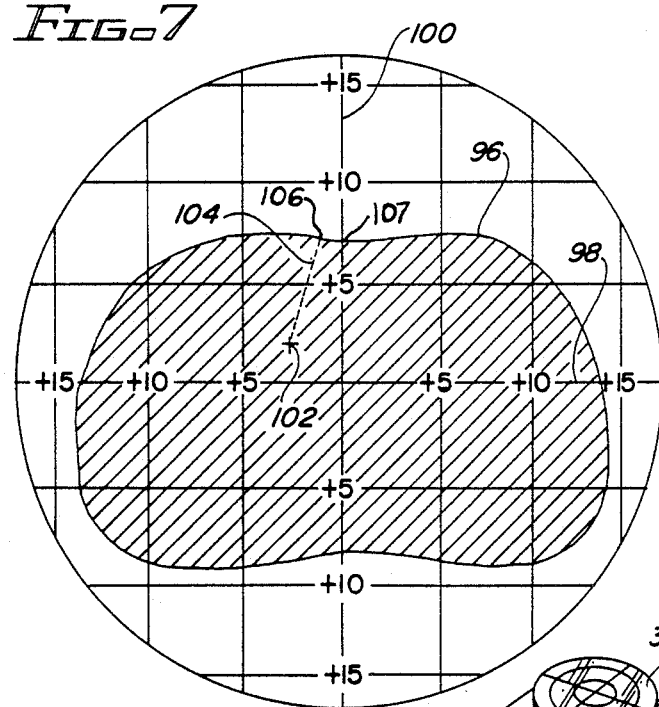
FIG. 10 is an illustration of a C.T. scanner imaging screen displaying a sectional scan through a patient's abdomen, with superimposed position coordinates

In order to practice the method of the present invention, a patient is scanned in conventional fashion to determine the location of the abnormal area, also referred to herein as the target area. An image, like that shown in FIG. 10, is displayed upon the C.T. scanner computer screen showing a cross-section of the patient's body. The outline of the displayed image is designated within FIG. 10 by reference numeral 96. By depressing a "grid" button on the monitor console, the computer screen can selectively superimpose an x-axis 98 and a y-axis 100 over the displayed image of the patient's body. Referring briefly to FIG. 5, y-axis 100 corresponds to the position of longitudinal reference beam 88 upon the patient's body. For purposes of explanation, it will be presumed that the computer-generated marker designated by reference numeral 102 within the cross-sectional image shown in FIG. 10 designates the tissue mass that is to be biopsied.

While viewing the computer generated image shown in FIG. 10, the physician determines the best straight line path lying within the sectioned plane of the patient's body to reach target 102 without injuring surrounding organs or blood vessels. For the sake of explanation, it will be presumed that the angled path indicated by dashed line 104 represents the selected insertion path for inserting a biopsy needle to reach target area 102. By using a cursor on the computer screen, the radiologist can mark both the target area 102 and the insertion site 106 at which the needle will be inserted. As shown in FIG. 10, insertion site 106 is the point on the outer surface of the patient's body which is intersected by selected insertion path 104. The C.T. scanner computer can then easily compute the distance from insertion site 106 to the point 107 at which the vertical reference axis, or y-axis 100 intersects the outer surface of the patient's body. The C.T. scanner computer can also be used to display the insertion angle that proposed path 104 forms with either x-axis 98 or y-axis 100; preferably, the insertion angle is determined relative to the x-axis 98, corresponding to the angle that the needle will form with a horizontal plane. In addition, the C.T. scanner computer is also capable of measuring and displaying the length of the path (i.e., insertion distance) from insertion site 106 to target area 102.

Once the radiologist has obtained the information set forth above, the radiologist locates the proposed insertion site upon the patient's body by starting at the intersection of longitudinal light beam 88 and the appropriate transverse beam 90 or 92, and measuring off on the patient's body (along the transverse beam) the distance indicated by the C.T. scanner computer between point 107 and entry site 106. It may be sufficient at this stage to simply mark the insertion site upon the patient's body with an indelible pen. However, to insure that the insertion site has been properly located, a 1 mm. radiopaque nipple marker is first placed on this point of the patient's body, and a second scan is performed to confirm that the radiopaque marker overlies the selected insertion site. The scanning table is then moved along its longitudinal axis by the distance separating transverse beams 90 and 92, thereby shifting the radiopaque marker from the transverse beam 90 to transverse beam 92. The indelible pen is then used to mark the position of the radiopaque marker, and the radiopaque marker is thereafter removed.

Figure 11:
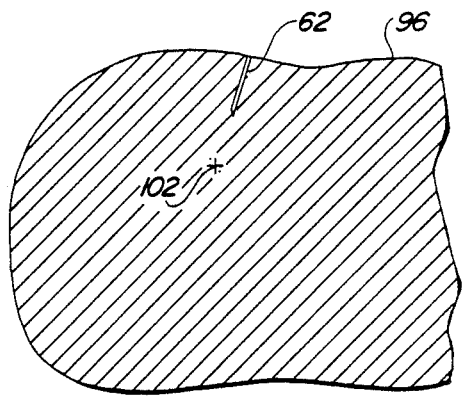
FIG. 11 is a second C.T. scanner computer screen image showing the tip of the biopsy needle after the same has been inserted into the patient toward the target area.

The biopsy needle 62 is then inserted into the guidance device, as shown in FIG. 1, and the needle support arm angle relative to planar base 22 is locked at the insertion angle indicated by the C.T. scanner computer. The user then supports guidance device 20 in close proximity to the patient's body, with the tip 76 of biopsy needle 62 directed toward insertion site 106. The user then views the circular bubble level 34 and adjusts the position of guidance device 20 until planar base 22 is essentially horizontal. Simultaneously, the user adjusts guidance device 20 until reference line 94 coincides with transverse reference beam; as noted above, the transverse reference beam initially strikes needle 62, and by maintaining the full length of needle 62 illuminated by the transverse reference beam, the user can be assured that needle 62 is kept within the scanned plane. Tip 76 of biopsy needle 62 is contacted against insertion site 106, and the user then notes the initial position of biopsy needle 62 relative to the graduated markings 78. The user then advances biopsy needle into the patient's body until the needle has been advanced to the measured insertion distance, as computed by the C.T. scanner computer. Depending upon the size of the lesion or target mass, and its distance from the skin, perhaps one intermediate scan may be desired to insure that needle 62 has not been deflected from, and is within, the selected plane and along the proper trajectory. FIG. 11 illustrates such an intermediate scan with biopsy needle 62 advanced midway toward target area 102.

Figure 12:
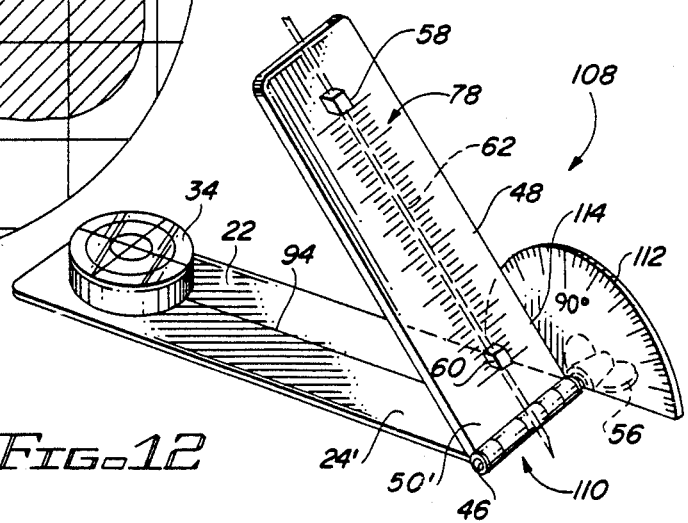
FIG. 12 is an alternate embodiment of a guidance device useful in practicing the present invention.

In FIG. 12, an alternate form of guidance device for practicing the method of the present invention is shown wherein components corresponding to those previously described in regard to FIGS. 1-4 are labeled With corresponding reference numerals. The principal difference between the guidance device 108 shown in FIG. 12 and guidance device 20 shown in FIGS. 1-3 is the manner in which needle support arm 48 is secured to planar base 22. As shown in FIG. 12. the lower end 50' is pivotally coupled to end 24' of planar base 22 by a hinged coupling 110, including hinge pin 46 and releasable locking wing nut 56. A protractor 112 extends perpendicularly from planar base 22 proximate end 24' thereof and adjacent side edge 114 of needle support arm 48 in order to indicate the relative angular relationship between needle support arm 48 and planar base 22. Needle guides 58 and 60 are secured to needle support arm 48 for releasably supporting needle 62. Guidance device 108 is otherwise used in the same manner as guidance device 20.

The guidance devices disclosed herein may easily be manufactured from molded plastic components and are easily assembled. The guidance device is relatively compact and may be packaged and stored in sterile form for ready access by physicians or other users. The guidance device may be quickly and easily locked at the desired angle. Since the guidance device disclosed herein is manually supported, the user can quickly position the guidance device for use adjacent the patient's body without the need to adjust a series of cranks, bearings, or arms in order to make the needle insertion.

Those skilled in the art Will now appreciate that a guidance method has been described to facilitate C.T. guided biopsy and fluid drainages in an accurate, easy and relatively prompt manner. Those skilled in the art will further appreciate that the longitudinal reference beam projected by the C.T. scanner defines a vertical plane, and that the transverse reference beams projected by the C.T. scanner also define vertical planes perpendicular to the vertical plane defined by the longitudinal reference beam. While the invention has been described with reference to preferred embodiment thereof, the description is for illustrative purposes only and is not to be construed as limiting the scope of the invention. Various modifications and changes may be made by those skilled in the art without departing from the true spirit and scope of the invention as defined by the appended claims, wherein the term catheter is intended to broadly designate biopsy needles, drainage catheters, or any other form of medical needle or tube.

As an example of one variation of the method disclosed herein, some C.T. scanners have a lighting system adapted to project a horizontal reference beam along the side of the patient's body in a horizontal plane. The plane of the horizontal reference beam corresponds with the x axes upon the scanned image. The present method may be practiced by computing the distance on the scanned image from the insertion site to the point at which the horizontal axis intersects the outer surface of the patient's body; thereafter. the intersection of the horizontal and transverse reference beams is located upon the patient's body, and the aforementioned distance is measured upon the patient's body along the transverse reference beam to locate the insertion site.

I claim:

1. A method of guiding a catheter toward a target area within a patient's body in conjunction with a C.T. scanner, the catheter having a piercing tip, the C.T. scanner being adapted to project at least one transverse reference beam of light across the patient's body to indicate the location of the vertical plane through which the patient's body has been scanned, said method comprising the steps of:
   (a) scanning the patient's body using the C.T. scanner to form a cross-sectional image of the target area within the patient's body:
   (b) positioning the catheter to lie within the plane of the transverse reference beam before inserting the piercing tip into the patient's body;
   (c) directing the piercing tip of the catheter at the target area; and
   (d) advancing the piercing tip of the catheter into the patient's body while maintaining the catheter within the plane of the transverse reference beam.

2. The method recited by claim 1 wherein the C.T. scanner is adapted to project a longitudinal reference beam along the central longitudinal axis of the C.T. scanner and upon the patient's body to indicate the vertical axis of the scanned cross-sectional image, and wherein the method further includes the steps of:
   (a) selecting an insertion path on the scanned cross-sectional image through which the catheter is to be guided;
   (b) measuring the distance upon the cross-sectional image from the intersection of the vertical axis of the scanned image with the outer surface of the patient's body to an insertion site on the outer surface of the patient's body which is intersected by the insertion path;
   (c) marking an insertion site upon the patient's body lying on the transverse reference beam at the measured distance from the longitudinal reference beam; and
   (d) inserting the piercing tip of the catheter at the marked insertion site upon the patient's body.

3. The method recited by claim 1 wherein the step of directing the piercing tip of the catheter at the target area includes the steps of:
   (a) selecting an insertion path on the scanned cross-sectional image through which the catheter is to be guided:
   (b) measuring the insertion angle which the selected insertion path forms relative to a horizontal axis of the cross-sectional image; and
   (c) maintaining the catheter at the measured insertion angle relative to a horizontal plane.

4. The method recited by claim 1 wherein the step of advancing the piercing tip of the catheter into the patient's body includes the steps of:
   (a) selecting an insertion path on the scanned cross-sectional image through which the catheter is to be guided;
   (b) measuring the insertion distance upon the cross-sectional image from the target area to an insertion site on the outer surface of the patient's body Which is intersected by the insertion path; and
   (c) advancing the catheter into the patient's body by the measured insertion distance.

5. A method of guiding a catheter toward a target area within a patient's body in conjunction with a C.T. scanner, the catheter having a piercing tip, the C.T. scanner being adapted to project at least one transverse reference beam of light across the patient's body to indicate the location of the vertical plane through which the patient's body has been scanned, the C.T. scanner being further adapted to project a longitudinal reference beam along the central longitudinal axis of the C.T. scanner to indicate the vertical axis of the scanned cross-sectional image, and wherein the method comprises the steps of:
   (a) scanning the patient's body using the C.T. scanner to form a cross-sectional image of the target area within the patient's body;
   (b) selecting an insertion path on the scanned cross-sectional image through which the catheter is to be guided;
   (c) measuring the distance upon the cross-sectional image from the intersection of the vertical axis of the scanned image with the outer surface of the patient's body to an insertion site on the outer surface of the patient's body which is intersected by the insertion path:
   (d) measuring the insertion angle which the selected insertion path forms relative to the horizontal axis of the cross-sectional image:
   (e) marking an insertion site upon the patient's body lying on the transverse reference beam at the measured distance from the longitudinal reference beam;
   (f) positioning the catheter to lie within the plane of the transverse reference beam before inserting the piercing tip into the patient's body;
   (g) maintaining the catheter at the measured insertion angle relative to a horizontal plane;
   (h) inserting the piercing tip of the catheter at the marked insertion site upon the patient's body: and
   (i) advancing the piercing tip of the catheter into the patient's body while maintaining the catheter within the plane of the transverse reference beam.

6. A method as recited by claim 5 wherein the step of advancing the piercing tip of the catheter into the patient's body includes the steps of:
   (a) measuring the insertion distance upon the cross-sectional image from the target area to an insertion site on the outer surface of the patient's body which is intersected by the insertion path; and
   (b) advancing the catheter into the patient's body by the measured insertion distance.

7. A method of locating an insertion site upon a patient's body in conjunction with a C.T. scanner, through which insertion site a catheter is to be guided toward a target area within the patient's body, the C.T. scanner being adapted to project at least one transverse reference beam of light across the patient's body to indicate the location of the vertical plane through which the patient's body has been scanned, the C.T. scanner being further adapted to project a longitudinal reference beam along the central longitudinal axis of the C.T. scanner to indicate the vertical axis of the scanned cross-sectional image, and wherein the method comprises the steps of:
   (a) scanning the patient's body using the C.T. scanner to form a cross-sectional image of the target area within the patient's body;
   (b) selecting an insertion path on the scanned cross-sectional image through which the catheter is to be guided;
   (c) measuring the distance upon the cross-sectional image from the intersection of the vertical axis of the scanned image with the outer surface of the patient's body to an insertion site on the outer surface of the patient's body which is intersected by the insertion path; and
   (d) marking the insertion site upon the patient's body lying on the transverse reference beam at the measured distance from the longitudinal reference beam.

* * * * *